United States Patent
Kim et al.

(10) Patent No.: US 11,649,414 B2
(45) Date of Patent: May 16, 2023

(54) SYNTHETIC VEGETABLE OIL AND ENVIRONMENTAL-FRIENDLY FLAME-RETARDANT HYDRAULIC OIL COMPOSITION INCLUDING THE SAME, AND PREPARATION METHOD THEREOF

(71) Applicant: HANVAL INC., Ulsan (KR)

(72) Inventors: Kwang Soon Kim, Seoul (KR); Dong Choon Lee, Chungcheongnam-do (KR); Young Uk Kwon, Seoul (KR)

(73) Assignee: HANVAL INC., Ulsan (KR)

( * ) Notice: Subject to any disclaimer, the term of this patent is extended or adjusted under 35 U.S.C. 154(b) by 0 days.

(21) Appl. No.: 17/601,422

(22) PCT Filed: Jan. 28, 2021

(86) PCT No.: PCT/KR2021/001135
§ 371 (c)(1),
(2) Date: Oct. 4, 2021

(87) PCT Pub. No.: WO2021/154004
PCT Pub. Date: Aug. 5, 2021

(65) Prior Publication Data
US 2022/0195327 A1    Jun. 23, 2022

(30) Foreign Application Priority Data

Jan. 31, 2020  (KR) .................. 10-2020-0012105
Jun. 12, 2020  (KR) .................. 10-2020-0071692

(51) Int. Cl.
*C10M 177/00*    (2006.01)
*C10M 105/36*    (2006.01)
(Continued)

(52) U.S. Cl.
CPC ........ *C10M 177/00* (2013.01); *C10M 105/36* (2013.01); *C10M 137/08* (2013.01);
(Continued)

(58) Field of Classification Search
CPC ........ C10M 177/00; C10M 2207/2835; C10M 105/38; C10N 2040/08; C10N 2070/00
(Continued)

(56) References Cited

U.S. PATENT DOCUMENTS 4,263,159 A * 4/1981 Berens ................. C10M 105/38
                                                    252/79
5,034,144 A * 7/1991 Ohgake ................ C10M 129/38
                                                    508/488
(Continued)

FOREIGN PATENT DOCUMENTS

JP    H0496996 A      3/1992
JP    2003049192      2/2003
(Continued)

*Primary Examiner* — Ellen M McAvoy
(74) *Attorney, Agent, or Firm* — Hanval Inc.

(57) ABSTRACT

The present disclosure relates to a synthetic vegetable oil and an environmental-friendly flame-retardant hydraulic oil composition including the same, and a preparation method thereof, and provides a method of preparing a glycerin-ester-based lubricating base oil through a catalyst-free and rinsing-free process, a glycerin-ester-based lubricating base oil that is a synthetic vegetable oil obtained by the method, and an environmental-friendly flame-retardant hydraulic oil composition that contains the glycerin-ester-based lubricating base oil and that is capable of reducing electricity consumption by 7 to 8% compared to mineral oil-based lubricating oils due to excellent flame retardancy (with self-extinguishing function) and lubricity.

6 Claims, 3 Drawing Sheets

(51) Int. Cl.
*C10M 137/08* (2006.01)
*C10N 30/02* (2006.01)
*C10N 40/08* (2006.01)
*C10N 70/00* (2006.01)

(52) U.S. Cl.
CPC ............... *C10M 2207/2835* (2013.01); *C10M 2223/043* (2013.01); *C10N 2030/02* (2013.01); *C10N 2040/08* (2013.01); *C10N 2070/00* (2013.01)

(58) Field of Classification Search
USPC .......................................................... 508/436
See application file for complete search history.

(56) References Cited

U.S. PATENT DOCUMENTS

| | | | | | |
|---|---|---|---|---|---|
| 5,145,593 | A | * | 9/1992 | Takashima | C10M 101/04 508/488 |
| 5,552,068 | A | * | 9/1996 | Griffith | C10M 137/08 508/436 |
| 5,580,482 | A | * | 12/1996 | Chasan | C10M 133/44 508/281 |
| 5,618,779 | A | * | 4/1997 | Klein | C10M 129/16 508/491 |
| 5,773,391 | A | * | 6/1998 | Lawate | C10M 135/24 508/491 |
| 6,160,144 | A | * | 12/2000 | Bongardt | C07C 69/52 554/224 |
| 6,361,711 | B1 | * | 3/2002 | Abe | C10M 169/041 508/474 |
| 6,551,523 | B1 | | 4/2003 | Schnur | |
| 2004/0259743 | A1 | * | 12/2004 | Butke | C10M 169/04 508/273 |

FOREIGN PATENT DOCUMENTS

| | | |
|---|---|---|
| JP | 2003252829 | 9/2003 |
| JP | 2008280500 | 11/2008 |
| JP | 2009523866 A | 6/2009 |
| JP | 2011001281 | 1/2011 |
| JP | 2013173940 | 9/2013 |
| KR | 960029441 | 8/1996 |
| KR | 20050084009 | 8/2005 |
| KR | 20080020442 | 3/2008 |
| KR | 20110012748 | 2/2011 |
| KR | 20110119322 | 11/2011 |
| KR | 20130038984 | 4/2013 |
| KR | 101292675 | 8/2013 |
| KR | 20140109853 | 9/2014 |
| KR | 20190047569 | 5/2019 |
| KR | 102156065 | 9/2020 |
| WO | 2010097920 A1 | 9/2010 |

* cited by examiner

SYNTHETIC VEGETABLE OIL AND ENVIRONMENTAL-FRIENDLY FLAME-RETARDANT HYDRAULIC OIL COMPOSITION INCLUDING THE SAME, AND PREPARATION METHOD THEREOF

CROSS-REFERENCE TO RELATED APPLICATIONS

This application is a U.S. national stage entry of International Application No. PCT/KR2021/001135, filed Jan. 28, 2021, which claims priority to Korean Application No. 10-2020-0012105, filed Jan. 31, 2020, and Korean Application No. 10-2020-0071692, filed Jun. 12, 2020, the entire disclosures of which are incorporated herein by reference.

TECHNICAL FIELD

The present disclosure relates to a synthetic vegetable oil and an environmental-friendly flame-retardant hydraulic oil composition including the same, and a preparation method thereof.

BACKGROUND ART

In the process of industrial development, emphasis on affinity for the natural environment and humans, energy reduction measures, and guarantee of stable operation of equipment are inevitably essential conditions, so the supply of lubricating oils that may more actively cope with these conditions have been demanded. However, it may be a very difficult task in the (mineral lubricating oil) lubricating oil industry (especially hydraulic oil) where a large amount of petroleum refined products is used. In the meantime, research using glycerine-esters and lubricating oils based on vegetable oils developed domestically and internationally has been reported. However, in the research, vegetable oil itself was used (Korean Laid-Open Patent Publication No. 1996-0029441), or various alcohols and fatty acids were used, but catalyst synthesis method was followed by washing with water (U.S. Pat. No. 6,551,523).

The most difficult thing in the lubricating oil using vegetable oil itself is that it cannot overcome stability defects against heat and oxidation due to the high content of unsaturated hydrocarbons that the vegetable oil has. Even though the content of unsaturated hydrocarbons is adjusted, by the catalyst used according to the ester synthesis method in the related art and washing treatment of alkaline materials with water, it is common for traces of residues (catalysts, alkali materials) to remain, and thus it causes a very bad effect of stability defects against hydrolysis and formation of foreign substances. Therefore, the limitations of eco-friendly lubricating oils using vegetable oil itself occur and the compatibility is not great.

In this respect, example embodiments of the present disclosure relate to a preparation process for providing a glycerin-ester and a hydraulic oil including the same, in which the glycerin ester is synthesized using fatty acid and glycerin derived from vegetable oils and through a catalyst-free and rinsing-free process, which not only dramatically improves issues arising in the process of using hydraulic oils (lubricating oils), with being further improved and developed in comparison with the related art, but also guarantees expansion of application areas as hydraulic oils and extension of a service life, and satisfies a tool life and energy savings.

DISCLOSURE OF INVENTION

Technical Subject

To solve the above-described problems, example embodiments of the present disclosure provide a method of preparing a glycerin-ester-based lubricating base oil which may synthesize an environmental-friendly vegetable glycerin ester using glycerin and fatty acid derived from vegetables, through a catalyst-free and rinsing-free synthesis process.

Example embodiments of the present disclosure provide a method of preparing of a flame-retardant hydraulic oil composition using the environmental-friendly vegetable glycerin-ester obtained by the method of preparing a glycerin-ester-based lubricating base oil according to the present disclosure, in which the flame-retardant hydraulic oil composition is environmental-friendly and flame-retardant, has a good affinity for a human body because biodegradation by microorganisms is possible, and has an energy saving effect even when equipment is driven.

To solve the above-described problems, example embodiments of the present disclosure provide a glycerin-ester-based lubricating base oil including a glycerin-ester which is an environmental-friendly synthetic vegetable oil using glycerin and fatty acid derived from vegetables, through a catalyst-free and rinsing-free synthesis process.

Example embodiments of the present disclosure provide an environmental-friendly flame-retardant hydraulic oil composition using the environmental-friendly vegetable glycerin-ester according to the present disclosure, in which the environmental-friendly flame-retardant hydraulic oil composition is environmental-friendly and flame-retardant, has a good affinity for a human body because biodegradation by microorganisms is possible, and is excellent in physical properties, so as to contribute to a substantial cost reduction because it has a low risk of fire due to its flame retardancy, as well as an energy saving effect, extension of a tool life, an increase in an efficiency of equipment operation, and a reduction in an equipment consumable replacement cycle, even when equipment is driven in industrial sites, and so as to respond to regulation of carbon emission.

However, aspects of the present disclosure are not limited to the one set forth herein, and other aspects not mentioned herein would be clearly understood by one of ordinary skill in the art from the following description.

Technical Solutions

According to an aspect, there is provided a method of preparing a glycerin-ester-based lubricating base oil including a step of adding a fatty acid-containing raw material and a glycerin-containing raw material to a reactor, and a step of synthesizing a glycerin-ester in an inert gas atmosphere and a reaction temperature of 100° C. to 350° C. in the reaction, wherein the method is a catalyst-free and rinsing-free process.

According to an example embodiment, the reaction temperature may have a plurality of temperature sections, and an amount of the inert gas to be added ranges from 10 liters to 1000 liters per minute, based on the synthesis amount of 10000 liters, and may be adjusted depending on the temperature sections.

According to an example embodiment, the reaction temperature may be raised to 50° C. when a free fatty acid (FFA) content is reduced by 50%, and the amount of the gas to be added may be increased by 50% or more when the FFA content is reduced by 50%.

According to an example embodiment, the step of synthesizing the glycerin-ester may terminate the synthesis when the FFA content is 1.0 or less or 0.5 or less.

According to an example embodiment, the reaction temperature may include at least one of a first temperature section of 100° C. to 180° C., a second temperature section of 200° C. to 230° C., and a third temperature section of 250° C. to 350° C.

According to an example embodiment, the amount of the inert gas to be added may include at least one of a first amount of 10 liters to 50 liters to be added per minute, a second amount of 50 liters to 150 liters to be added per minute, and a third amount of 150 liters to 1000 liters to be added per minute, based on the synthesis amount of 10000 liters.

According to an example embodiment, the step of performing the synthesis process may be carried out at an atmospheric pressure (760 mmHg) to a reduced pressure (360 mmHg).

According to an example embodiment, the fatty acid-containing raw material may be extracted from a natural vegetable oil, and may contain one or more of C10 to C22 fatty acids.

According to an example embodiment, a mass ratio of first fatty acid to the other fatty acids in the fatty acid-containing raw material may range from 99:1 to 1:99 or 99:1 to 75:25.

According to an example embodiment, the fatty acid-containing raw material may contain a unsaturated fatty acid of 75% by weight (wt %) or more in the fatty acid-containing raw material.

According to an example embodiment, the fatty acid-containing raw material may contain a polyunsaturated fatty acid of 20 wt % or less in the fatty acid-containing raw material.

According to an example embodiment, the fatty acid-containing raw material may contain a C18 unsaturated fatty acid of 75 wt % or more or a C18 polyunsaturated fatty acid of 20 wt % or less in the fatty acid-containing raw material.

According to an example embodiment, the glycerin-ester may be represented by the following Formula 1:

[Formula 1]

In Formula 1, $R_1$, $R_2$ and $R_3$ are each a C8 to C20 saturated or unsaturated fatty acid residue.

According to another aspect, there is provided a method of preparing a flame-retardant hydraulic oil composition including a step of synthesizing a glycerin-ester using the method for preparing a glycerin-ester-based lubricating base oil according to the present disclosure and a step of preparing a hydraulic oil composition by blending the glycerin-ester and a flame-retardant additive.

According to an example embodiment, the flame-retardant additive may be included in an amount of 0.01 wt % to 10.0 wt % in the flame-retardant hydraulic oil.

According to an example embodiment, the flame-retardant additive may be a phosphor-based or halogen-based flame-retardant additive, and the phosphor-based or halogen-based flame-retardant additive may include one or more of tricresyl phosphate, tributyl phosphate, Tris (β-chloroethyl) phosphate, Tris (β-chloropropyl) phosphate, Tris (dichloropropyl) phosphate, trioctyl phosphate, triphenyl phosphate, octyl diphenyl phosphate, Tris (isopropylphenyl) Phosphate and tributoxyethyl phosphate.

According to an example embodiment, the flame-retardant hydraulic oil may further include one or more functional additives prepared from the group of an antioxidant, an anti-load and anti-abrasive enhancer, a thickener, a corrosion inhibitor and an antifoaming agent, and the additive may be contained in an amount of 0.1 wt % to 10 wt % in the flame-retardant hydraulic oil individually or entirely.

According to an example embodiment, the flame-retardant hydraulic oil may have a kinematic viscosity of 10 $mm^2/sec$ to 200 $mm^2/sec$ at 40° C.

According to an example embodiment, the glycerin-ester-based lubricating base oil may include two or more types, when two or more types of the glycerin-ester-based lubricating base oil are included, a mass ratio of one glycerin-ester-based lubricating base oil to the other glycerin-ester-based lubricating base oil may range from 90:10 to 75:25 or 90:10 to 50:50.

According to another aspect, there is provided a glycerin-ester-based lubricating base oil including a glycerin-ester formed by a reaction of glycerin with a fatty acid-containing raw material that contains one or more of C10 to C22 fatty acids and that is extracted from a natural vegetable oil.

According to an example embodiment, the glycerin-ester-based lubricating base oil may be obtained through a rinsing-free process by reacting the fatty acid-containing raw material with the glycerin under a catalyst-free condition in an inert gas atmosphere and at a reaction temperature of 100° C. to 350° C.

According to an example embodiment, a mass ratio of first fatty acid to the other fatty acids in the fatty acid-containing raw material may range from 99:1 to 1:99 or 99:1 to 75:25.

According to an example embodiment, the fatty acid-containing raw material may have a mass ratio of C10 to C12 fatty acids of 75 wt % or more for a synthesis of a low-viscosity glycerin-ester-based raw material having a kinematic viscosity of 20 $mm^2/sec$ or lower, and a mass ratio of C18 to C20 fatty acids of 70 wt % or more for a synthesis of a high-viscosity glycerin-ester-based raw material having a kinematic viscosity of 30 $mm^2/sec$ or higher.

According to an example embodiment, the fatty acid-containing raw material may contain a monounsaturated fatty acid of 75 wt % or more in the fatty acid-containing raw material.

According to an example embodiment, the fatty acid-containing raw material may contain a polyunsaturated fatty acid of 20 wt % or less in the fatty acid-containing raw material.

According to an example embodiment, the fatty acid-containing raw material may contain a C18 monounsaturated fatty acid of 75 wt % or more or a C18 polyunsaturated fatty acid of 20 wt % or less in the fatty acid-containing raw material.

According to an example embodiment, the glycerin-ester-based lubricating base oil may have an FFA content (%) of 1.0 or less or 0.5 or less.

According to an example embodiment, the glycerin-ester-based lubricating base oil may have a kinematic viscosity of 10 mm²/sec to 1000 mm²/sec at 40° C.

According to an example embodiment, the glycerin-ester may be represented by the following Formula 1:

[Formula 1]

In Formula 1, $R_1$, $R_2$ and $R_3$ are each a C8 to C20 saturated or unsaturated fatty acid residue.

According to another aspect, there is provided an environmental-friendly flame-retardant hydraulic oil composition including a glycerin-ester-based lubricating base oil; and a flame-retardant additive, wherein the glycerin-ester-based lubricating base oil contains a glycerin-ester formed by a reaction of glycerin with a fatty acid-containing raw material that contains one or more of C10 to C22 fatty acids and that is extracted from a natural vegetable oil.

According to an example embodiment, the glycerin-ester-based lubricating base oil may include two or more types, when two or more types are included, a mass ratio of one glycerin-ester-based lubricating base oil to the other glycerin-ester-based lubricating base oils may range from 90:10 to 75:25 or 90:10 to 50:50.

According to an example embodiment, the flame-retardant hydraulic oil composition may have a kinematic viscosity of 10 mm²/sec to 200 mm²/sec at 40° C.

According to an example embodiment, the flame-retardant additive may be included in an amount of 0.01 wt % to 10 wt % in the flame-retardant hydraulic oil composition According to an example embodiment, the flame-retardant additive may be a phosphor-based or halogen-based flame-retardant additive, and the phosphor-based or halogen-based flame-retardant additive may include at least one of tricresyl phosphate, tributyl phosphate, Tris (β-chloroethyl) phosphate (Tris (βphosphate)), (Tris β-chloropropyl) phosphate (Tris (βphosphate)), Tris (dichloropropyl) phosphate, trioctyl phosphate, triphenyl phosphate, octyl diphenyl phosphate, Tris (isopropylphenyl) Phosphate and tributoxyethyl phosphate.

According to an example embodiment, at least one of an antioxidant, an anti-load and anti-abrasive enhancer, a thickening and viscosity index enhancer, a pour point depressant, and a corrosion inhibitor may be further included.

According to an example embodiment, the antioxidant may be included in an amount of 0.1 wt % to 7 wt % in the flame-retardant hydraulic oil composition.

According to an example embodiment, the antioxidant may contain at least one of phenylnaphthylamine-based compounds, aromatic amine-based compounds, phenol-based compounds, phosphate ester-based compounds, metal salts of phosphate ester, and sulfur-based compounds.

According to an example embodiment, the thickening and viscosity index enhancer may be included in an amount of 0.01 wt % to 5 wt % in the flame-retardant hydraulic oil composition, and the thickening and viscosity index enhancer may contain at least one of olefin copolymer, polybutene, polyisobutylene, polymethacrylate, polyacrylate, and ethylene propylene copolymer.

According to an example embodiment, the thickening and viscosity index enhancer may have a molecular weight of 300 to 10000.

According to an example embodiment, the anti-load and anti-abrasive additive may be included in an amount of 0.01 wt % to 7 wt % in the environmental-friendly flame-retardant hydraulic oil composition, and may include an amine salt-based compound of phosphate ester represented by Formula 2:

[Formula 2]

In Formula 2, R represents hydrogen or a C1 to C10 alkyl or aryl type hydrocarbon compound, X represents hydrogen or C1 to C4 hydrocarbon, and n is an integer from 1 to 10.

EFFECTS

Example embodiments of the present disclosure may provide a method of preparing a glycerin-ester-based lubricating base oil through a catalyst-free and rinsing-free process, and the method may provide an environmental-friendly lubricating base oil and a hydraulic oil including the same by synthesizing synthetic vegetable oils that do not contain any residual catalysts or residual alkaline materials. Furthermore, example embodiments of the present disclosure may provide an environmental-friendly hydraulic oil composition that is excellent in flame retardancy (low risk of fire), lubricity, heat/oxidation stability, and other physical properties, using the glycerin-ester-based lubricating base oil.

Example embodiments of the present disclosure may provide an environmental-friendly lubricating base oil by synthesizing synthetic vegetable oils with little or no residual catalysts or residual alkali materials, through a catalyst-free and rinsing-free process, and provide an environmental-friendly hydraulic oil composition that is excellent in flame retardancy (low risk of fire), lubricity, heat/oxidation stability, and other physical properties, using the glycerin-ester-based lubricating base oil.

Example embodiments of the present disclosure may provide a flame-retardant hydraulic oil composition that may have a good affinity for a human body due to a hydraulic oil used in equipment biodegradable by microorganisms, may reduce an amount of electricity consumed during driving of the equipment to support a stable contribution to carbon credits, may be excellent in driving of the equipment as well as a cost reduction caused by an energy reduction, and may significantly reduce a risk of fire by imparting flame retardancy.

BEST MODE FOR CARRYING OUT THE INVENTION

Hereinafter, example embodiments of the present disclosure will be described with reference to the accompanying drawings. When it is deemed that detailed description related to a related known function or configuration they may make the purpose of the present disclosure unnecessarily ambiguous in describing the present disclosure, the detailed description will be omitted here. Also, terms used herein are defined to appropriately describe the example embodiments and thus may be changed depending on a user, the intent of an operator, or a custom of a field to which the present disclosure pertains. Accordingly, the terms must be defined based on the following overall description of this specification. Like reference numerals present in the drawings refer to the like elements throughout.

Throughout the specification, when one part "includes" or "comprises" one component, the part does not exclude other components but may further include the other components, unless otherwise specified.

Throughout the specification, when one part "includes" or "comprises" one component, the part does not exclude other components but may further include the other components.

The present disclosure relates to a method of preparing a glycerin-ester-based lubricating base oil, and more specifically may provide a method of preparing a fatty acid glycerin-ester-based lubricating base oil by using glycerin and fatty acid extracted from a natural vegetable oil through a catalyst-free and rinsing-free process.

According to an example embodiment, the method of preparing the glycerin-ester-based lubricating base oil may include a step of adding a fatty acid-containing raw material and a glycerin-containing raw material to a reactor, and a step of synthesizing a glycerin-ester in the reaction.

According to an example embodiment, glycerin in the glycerin-containing raw material may be a material generally known in the technical field of the present disclosure, and for example may be obtained as a by-product in various industrial processes such as the production of biodiesel, or may be applied to various fields ranging from cosmetics and pharmaceuticals. In the step of added to the reactor, glycerin may have a purity of 95% or higher for an excellent synthesis result.

According to an example embodiment, fatty acid in the fatty acid-containing raw material may be extracted from a natural vegetable oil, and may contain one or more of C10 to C22 fatty acids. The fatty acid may contain saturated and/or unsaturated (monounsaturated and polyunsaturated) fatty acid, and the unsaturated fatty acid may contain cis- and/or trans-unsaturated fatty acid.

More specifically, the unsaturated fatty acid of the fatty acids may be applied without limitation as long as a glycerin-ester-based lubricating base oil may be provided, and for example, may include pentadecylic acid (pentadecanoic acid), arachidonic acid, myristic acid (myristoleic acid), palmitoleic acid, sapienic acid, elaidic acid, vaccenic acid; omega-9 fatty acid such as oleic acid (monounsaturated omega-9 fatty acid), eicosenoic acid (monounsaturated omega-9 fatty acid), and erucic acid (monounsaturated omega-9 fatty acid); omega-6 fatty acid such as arachidonic acid (polyunsaturated omega-6), eicosenoic acid (omega-6 fatty acid, eicosatrienoic acid, 11,14,17-eicosatrienoic acid) linoleic acid (polyunsaturated omega-6 fatty acid), and lino-elaidic acid (omega-6 trans fatty acid); and omega-7 fatty acid (monounsaturated); and the like.

The fatty-acid-containing raw material may contain C10 to C22 fatty acid alone or in combination in order to obtain various kinematic viscosity grades for use as a lubricating base oil. In other words, the fatty acid-containing raw material and glycerin-containing raw material may be added to a reactor by adjusting a content ratio of glycerin and fatty acid and/or types and/or compositions (for example, alone or in combination) of fatty acid, in order to obtain a desired kinematic viscosity of the lubricating base oil.

For example, when the fatty acid-containing raw material contains two or more of fatty acids, a mass ratio of first fatty acid to the other fatty acids may range from 99:1 to 1:99, 99:1 to 75:25, or 90:10 to 80:20. For example, the fatty acid-containing raw material has a C10 to C12 fatty acid mass ratio of 75 wt % or more for a synthesis of a low-viscosity glycerin-ester-based raw material having a kinematic viscosity of 20 mm$^2$/sec or lower, and a C18 to C20 fatty acid mass ratio of 70 wt % or more for a synthesis of a high-viscosity glycerin-ester-based raw material having a kinematic viscosity of 30 mm$^2$/sec or higher. By adjusting the mass ratio, stability against heat and oxidation, quality, and manufacturing cost of the lubricating base oil may be improved.

For example, the fatty acid-containing raw material may contain a monounsaturated fatty acid of 75 wt % or more or 75 wt % to 80 wt % in the fatty acid-containing raw material or a polyunsaturated fatty acid of 20 wt % or less or 15% or less by weight in the fatty acid-containing raw material, in order to provide a lubricating base oil which has a high-quality and which maintains stability against heat and oxidation. Preferably, in order to obtain a lubricating base oil which is expensive and has the most efficient quality, a C18 fatty acid (oleic acid and linoleic acid) may be used as the fatty acid. At this time, the total amount of the C18 fatty acid may be adjusted to exceed 90%, but the linoleic acid may have a content of 15% or less in order to maintain stability against heat and oxidation.

The glycerin to the fatty acid-containing raw material may be added to a reactor in a ratio (mass ratio) of 9.5:90.5 to 16.0:84.

According to an example embodiment, in the step of synthesizing the glycerin-ester, a step of adding glycerin-containing raw material and the fatty acid-containing raw material to a reactor, and synthesizing a glycerin-ester in an inert gas atmosphere and at a reaction temperature of 100° C. to 350° C. in the reaction may be performed.

The inert gas may include one or more of helium (He), nitrogen (N$_2$), argon (Ar), neon (Ne) and xenon (Xe), and when the mixed gas is formed, nitrogen to the other gases may be supplied at a flow rate (or an amount to be added) of 1:1 to 1:0.1. The inert gas may be filled or flowed into a reactor before adding raw materials, and may be continuously supplied into the reactor during synthesis.

An amount of the inert gas to be added ranges from 10 liters to 1000 liters per minute, based on the synthesis amount of 10000 liters, and is adjusted depending on the temperature sections described blow.

In the step of synthesizing the glycerin-ester, in order to improve yield of the lubricating base oil and reduce the synthesis time, synthesis may be performed by setting a plurality of temperature sections, and an amount of inert gas to be added may also be adjusted depending on the plurality of temperature sections. The plurality of temperature rise sections may be determined by checking a degree of synthesis, and the degree of synthesis may be determined by a free fatty acid (FFA) content. That is, the reaction temperature may be raised to 10° C. or higher; 30° C. or higher; 50° C. or higher; preferably 50° C. when the FFA content is reduced by 50%, and the amount of the inert gas to be added may be increased by 50% or more when the FFA content is reduced by 50%. The step of synthesizing the glycerin-ester may terminate the synthesis when the FFA content is 1.0 or less or 0.5 or less.

For example, the reaction temperature may include at least one of a first temperature section of 100° C. to 180° C., a second temperature section of 200° C. to 230° C., and a third temperature section of 250° C. to 350° C.

For example, the amount of the inert gas to be added may include at least one of a first amount of 10 liters to 50 liters to be added per minute, a second amount of 50 liters to 150 liters to be added per minute, and a third amount of 150 liters to 1000 liters to be added per minute, based on the synthesis amount of 10000 liters.

The step of performing the synthesis process may be carried out at an atmospheric pressure (760 mmHg) to a reduced pressure (350 mmHg).

According to an example embodiment, the glycerin-ester-based lubricating base oil may have an FFA content (%) of 1.0 or less or 0.5 or less and have a kinematic viscosity of 10 mm²/sec or higher or 10 mm²/sec to 200 mm²/sec.

According to an example embodiment, the glycerin-ester-based lubricating base oil may contain a triglyceride type glycerin-ester represented by the following Formula 1:

[Formula 1]

In Formula 1, $R_1$, $R_2$ and $R_3$ are each a C8 to C20 saturated or unsaturated fatty acid residue.

Example embodiments of the present disclosure may provide a method of preparing the glycerin-ester-based lubricating base oil according to the present disclosure, or a method of preparing a flame-retardant hydraulic oil composition using the glycerin-ester-based lubricating base oil. That is, the method of preparing the flame-retardant hydraulic oil composition may provide an environmental-friendly flame-retardant hydraulic oil composition by using a method of preparing a glycerin-ester-based lubricating base oil from the vegetable oils which may be decomposed by microorganisms and which emphasizes affinity for humans and equipment, or a glycerin-ester-based lubricating base oil through a catalyst-free and rinsing-free process.

According to an example embodiment, the method of preparing the flame-retardant hydraulic oil composition may include a step of synthesizing the glycerin-ester according to the present disclosure and a step of preparing a hydraulic oil composition by blending the glycerin-ester-based lubricating base oil and a flame-retardant additive.

According to an example embodiment, in the step of preparing the hydraulic oil composition, the glycerin-ester-based lubricating base oil may be included alone or in a mixture of two or more types, when two or more types of the glycerin-ester-based lubricating base oils are included, a mass ratio of one glycerin-ester-based lubricating base oil to the other glycerin-ester-based lubricating base oil may range from 90:10 to 75:25 or 90:10 to 50:50. When the mass ratio is included in the above range, by improving the quality and biodegradability of the flame-retardant hydraulic oil, a more efficient environmental-friendly flame-retardant hydraulic oil may be provided.

According to an example embodiment, the flame-retardant additive may be included in an amount of 0.01 wt % to 10 wt % in the flame-retardant hydraulic oil, and when the flame-retardant additive is included in the above range, it is preferable because it is possible to more smoothly respond to a risk of fire by improving flame retardancy.

The flame-retardant additive may be a phosphor-based or halogen-based flame-retardant additive, and may include one or more of tricresyl phosphate, tributyl phosphate, Tris (β-chloroethyl) phosphate, Tris (β-chloropropyl) phosphate, Tris (dichloropropyl) phosphate, trioctyl phosphate, triphenyl phosphate, octyl diphenyl phosphate, Tris (isopropylphenyl) Phosphate and tributoxyethyl phosphate.

According to an example embodiment, in the step of preparing the hydraulic oil, one or more functional additives prepared from the group of an antioxidant, an anti-load and anti-abrasive enhancer, a thickener, a corrosion inhibitor and an antifoaming agent may be further added.

The functional additive may be included in an amount of 0.1 wt % to 10 wt % in the flame-retardant hydraulic oil individually or entirely. An amount of the additive may be added in an appropriate amount in consideration of the appropriate combination with the glycerin-ester-based lubricating base oil, and occurrence of quality reduction, discoloration, biodegradability deterioration, viscosity drop, etc. of the flame-retardant hydraulic oil due to the additive.

The antioxidant may include one or more of phenylnaphthylamine-based, aromatic amine-based, such as alkylated diphenylamine, phenol-based, phosphate ester-based and metal salts (Zn-DTP) of phosphate ester, and sulfur-based compounds, but not limited thereto. Preferably, the antioxidant may be phenylnaphylamine-based.

The antioxidant may be included in an amount of 0.01 wt % to 10.0 wt %, preferably 0.3 wt % to 4.0 wt % in the flame-retardant hydraulic oil. When the amount of the antioxidant is included in the above range, a suitable antioxidation effect may be obtained, and the occurrence of problems such as inhibition of environmental friendliness (biodegradability and fish toxicity) due to an increase in the amount added may be prevented or reduced.

The thickener may be a viscosity enhancer and a viscosity index enhancer, and may include one or more of olefin copolymers of styrene-hydrocarbon polymers such as styrene-butadiene copolymer and styrene-maleate ester copolymer, polybutene, polyisobutylene, and polymethacrylate, polyacrylate, ethylene-propylene copolymer, but not limited thereto.

A molecular weight of the thickener may be 300 to 10000 in consideration of flame retardancy and environmental friendliness, and the like. The thickener may be included in an amount of 0.01 wt % to 10.0 wt % in the flame-retardant hydraulic oil. When the molecular weight of the thickener is included in the above range, a hydraulic oil having an appropriate viscosity may be provided.

The anti-abrasive additive may include one or more of an amine salt of phosphate ester, aryl phosphate-based, metal salts of phosphate ester, and sulfide additives, but not limited thereto. Preferably, the anti-abrasive additive may be an amine salt of phosphate ester.

The anti-abrasive additive may range from 0.01 wt % to 7.0 wt % or 0.1 wt % to 2.0 wt % in the flame-retardant hydraulic oil. When the amount is included in the above range, while hydraulic equipment is running, excessive wear of cylinders, pumps, or the like may be prevented to improve a life of equipment and may reduce overheating caused by wear.

If necessary, corrosion inhibitors (an azo (azole)-based non-ferrous corrosion inhibitor, a succinic ester type ferrous corrosion inhibitor, a sulfonate (metal-sulfonate)-based corrosion inhibitor, etc.), anti-foaming agents (silicon type, alcohol type, amine type, or polymethacrylate anti-foaming agents), and other modifiers may be further added, and these amounts may be added in consideration of an appropriate amount and a combination between each component as long as it does not deviate from the aspect of the present disclosure.

Example embodiments of the present disclosure relate to a glycerin-ester-based lubricating base oil, and according to an example embodiment, the glycerin-ester-based lubricating base oil may be a glycerin-ester-based lubricating base oil of fatty acid obtained by using glycerin and fatty acid extracted from a natural vegetable oil through a catalyst-free and rinsing-free process.

According to an example embodiment, in a method of preparing the glycerin-ester-based lubricating base oil a glycerin ester may be synthesized as a synthetic vegetable oil by using fatty acid and glycerin derived from vegetable oils, and may be provided through a catalyst-free and rinsing-free process, which not only dramatically improves the problems arising in the process of using hydraulic oils (lubricating oil), but also expands application area as hydraulic oils, guarantees an extension of a service life, and satisfies a tool life and energy savings.

According to an example embodiment, the method of preparing the glycerin-ester-based lubricating base oil may include a step of adding a fatty acid-containing raw material and a glycerin-containing raw material to a reactor, and a step of synthesizing a glycerin-ester in the reaction.

According to an example embodiment, glycerin in the glycerin-containing raw material may be a material generally known in the technical field of the present disclosure, and for example may be obtained as a by-product in various industrial processes such as the production of biodiesel, or may be applied to various fields ranging from cosmetics and pharmaceuticals. In the step of added to the reactor, glycerin may have a purity of 95% or higher for an excellent synthesis result.

According to an example embodiment, fatty acid in the fatty acid-containing raw material may be extracted from a natural vegetable oil, and may contain one or more of C10 to C22 fatty acids. The fatty acid may contain saturated and/or unsaturated (monounsaturated and polyunsaturated) fatty acid, and the unsaturated fatty acid may contain cis- and/or trans-unsaturated fatty acid.

More specifically, the unsaturated fatty acid of the fatty acids may be applied without limitation as long as a glycerin-ester-based lubricating base oil may be provided, and for example, may include pentadecylic acid (pentadecanoic acid), arachidonic acid, myristic acid (myristoleic acid), palmitoleic acid, sapienic acid, elaidic acid, vaccenic acid; omega-9 fatty acid such as oleic acid (monounsaturated omega-9 fatty acid), eicosenoic acid (monounsaturated omega-9 fatty acid), and erucic acid (monounsaturated omega-9 fatty acid); omega-6 fatty acid such as arachidonic acid (polyunsaturated omega-6), eicosenoic acid (omega 6 fatty acid, eicosatrienoic acid, 11,14,17-eicosatrienoic acid) linoleic acid (polyunsaturated omega-6 fatty acid), and linoelaidic acid (omega-6 trans fatty acid); and omega-7 fatty acid (monounsaturated); and the like.

The fatty-acid-containing raw material may contain C10 to C22 fatty acid alone or in combination in order to obtain various kinematic viscosity grades for use as a lubricating base oil. In other words, the fatty acid-containing raw material and glycerin-containing raw material may be added to a reactor by adjusting a content ratio of glycerin and fatty acid and/or types and/or compositions (for example, alone or in combination) of fatty acid, in order to obtain a desired kinematic viscosity of the lubricating base oil.

For example, when the fatty acid-containing raw material contains two or more of fatty acids, a mass ratio of first fatty acid to the other fatty acids may range from 99:1 to 1:99, 99:1 to 75:25, or 90:10 to 80:20. For example, the fatty acid-containing raw material has a C10 to C12 fatty acid mass ratio of 75 wt % or more for a synthesis of a low-viscosity glycerin-ester-based raw materials having a kinematic viscosity of 20 mm$^2$/sec or lower, and a C18 to C20 fatty acid mass ratio of 70 wt % or more for a synthesis of a high-viscosity glycerin-ester-based raw material having a kinematic viscosity of 30 mm$^2$/sec or higher. By adjusting the mass ratio, stability against heat and oxidation, quality, and manufacturing cost of the lubricating base oil may be improved.

For example, the fatty acid-containing raw material may contain a monounsaturated fatty acid of 75 wt % or more or 75 wt % to 80 wt % in the fatty acid-containing raw material or a polyunsaturated fatty acid of 20 wt % or less or 15 wt % or less in the fatty acid-containing raw material, in order to provide a lubricating base oil which has a high-quality and which maintains stability against heat and oxidation. Preferably, in order to obtain a lubricating base oil which is expensive and has the most efficient quality, a C18 fatty acid (oleic acid and linoleic acid) may be used as the fatty acid. At this time, the total amount of the C18 fatty acid may be adjusted to exceed 90%, but the linoleic acid may have a content of 15% or less in order to maintain stability against heat and oxidation.

The glycerin to the fatty acid-containing raw material may be added to a reactor in a ratio (mass ratio) of 9.5:90.5 to 16.0:84.

According to an example embodiment, in the step of synthesizing the glycerin-ester, a step of adding glycerin-containing raw material and the fatty acid-containing raw material to a reactor, and synthesizing a glycerin-ester in an inert gas atmosphere and at a reaction temperature of 100° C. to 350° C. in the reaction may be performed.

The inert gas may include at least one or more of helium (He), nitrogen (N$_2$), argon (Ar), neon (Ne) and xenon (Xe), and when the mixed gas is formed, nitrogen to the other gases may be supplied at a flow rate (or an amount to be added) of 1:1 to 1:0.1. The inert gas may be filled or flowed into a reactor before adding raw materials, and may be continuously supplied into the reactor during synthesis.

An amount of the inert gas to be added ranges from 10 liters to 1000 liters per minute, based on the synthesis amount of 10000 liters, and is adjusted depending on the temperature sections described blow.

In the step of synthesizing the glycerin-ester, in order to improve yield of the lubricating base oil and reduce the synthesis time, synthesis may be performed by setting a plurality of temperature sections, and an amount of inert gas to be added may also be adjusted depending on the plurality of temperature sections. The plurality of temperature rise sections may be determined by checking a degree of synthesis, and the degree of synthesis may be determined by an FFA content. That is, the reaction temperature may be raised to 10° C. or higher; 30° C. or higher; 50° C. or higher; preferably 50° C. when the FFA content is reduced by 50%, and the amount of the gas to be added may be increased by 50% or more when the FFA content is reduced by 50%. The step of synthesizing the glycerin-ester may terminate the synthesis when the FFA content (%) is 1.0 or less or 0.5 or less.

For example, the reaction temperature may include at least one of a first temperature section of 100° C. to 180° C., a second temperature section of 200° C. to 230° C., and a third temperature section of 250° C. to 350° C.

For example, the amount of the inert gas to be added may include at least one of a first amount of 10 liters to 50 liters to be added per minute, a second amount of 50 liters to 150 liters to be added per minute, and a third amount of 150 liters to 1000 liters to be added per minute, based on the synthesis amount of 10000 liters.

The step of performing the synthesis process may be carried out at an atmospheric pressure (760 mmHg) to a reduced pressure (350 mmHg).

According to an example embodiment, the glycerin-ester-based lubricating base oil may have an FFA content (%) of 1.0 or less or 0.5 or less and have a kinematic viscosity of 10 mm$^2$/sec or higher or 10 mm$^2$/sec to 200 mm$^2$/sec.

According to an example embodiment, the glycerin-ester-based lubricating base oil may contain a triglyceride type glycerin-ester represented by the following Formula 1:

[Formula 1]

In Formula 1, $R_1$, $R_2$ and $R_3$ are each a C8 to C20 saturated or unsaturated fatty acid residue.

Example embodiments of the present disclosure relate to a flame-retardant hydraulic oil composition including the glycerin-ester-based lubricating base oil to according to the present disclosure, and according to an example embodiment, the flame-retardant hydraulic oil composition may be an environmental-friendly flame-retardant hydraulic oil composition, and by using a glycerin-ester-based lubricating base oil from the vegetable oils which may be decomposed by microorganisms and which emphasizes affinity for humans and equipment, or a glycerin-ester-based lubricating base oil through a catalyst-free and rinsing-free process, the composition has a good affinity for a human body because biodegradation by microorganisms is possible, and has excellent physical properties, so that it has a low risk of fire due to its flame retardancy, as well as an energy saving effect, extension of a tool life, an increase in an efficiency of equipment operation, and a reduction in an equipment consumable replacement cycle, even when equipment is driven in industrial sites.

According to an example embodiment, the flame-retardant hydraulic oil composition may include a glycerin-ester-based lubricating base oil and a flame-retardant additive, and further may include a functional additive.

According to an example embodiment, the glycerin-ester-based lubricating base oil may be included alone or in a mixture of two or more types, when two or more types of the glycerin-ester-based lubricating base oil are included, a mass ratio of one glycerin-ester-based lubricating base oil to the other glycerin-ester-based lubricating base oils may range from 90:10 to 75:25 or 90:10 to 50:50. When the mass ratio is included in the above range, by improving the quality and biodegradability of the flame-retardant hydraulic oil composition, a more efficient environmental-friendly flame-retardant hydraulic oil composition may be provided.

The glycerin-ester-based lubricating base oil may be included in an amount of 50 wt % or more; 60 wt % or more; 80 wt % or more; 90 wt % or more; 90 wt % to less than 100 wt % in the flame-retardant hydraulic oil composition.

According to an example embodiment, the flame-retardant additive may be included in an amount of 0.01 wt % to 10 wt % in the flame-retardant hydraulic oil composition, and when the flame-retardant additive is included in the above range, it is preferable because it is possible to more smoothly respond to a risk of fire by improving flame retardancy.

The flame-retardant additive may be a phosphor-based or halogen-based flame-retardant additive, and the phosphor-based or halogen-based flame-retardant additive may include at least one or more of tricresyl phosphate, tributyl phosphate, Tris (β-chloroethyl) phosphate (Tris (βphosphate)), Tris (β-chloropropyl) phosphate (Tris (βphosphate)), Tris (dichloropropyl) phosphate, trioctyl phosphate, triphenyl phosphate, octyl diphenyl phosphate, Tris (isopropylphenyl) Phosphate and tributoxyethyl phosphate, but not limited thereto.

According to an example embodiment, the functional additive may include at least one or more of a flame-retardant additive, an antioxidant, an anti-load and anti-abrasive enhancer, a thickening and viscosity index enhancer, a corrosion inhibitor and other modifiers.

The functional additive may be included in an amount of 0.1 wt % to 10 wt % in the flame-retardant hydraulic oil composition individually or entirely. An amount of the additive may be added in an appropriate amount in consideration of the appropriate combination with the glycerin-ester-based lubricating base oil, and occurrence of a reduction in environmental friendliness (biodegradability and fish toxicity), quality reduction, discoloration, viscosity drop, etc. of the hydraulic oil due to the additive.

According to an example embodiment, the antioxidant may be included in an amount of 0.1 wt % to 7.0 wt % in the flame-retardant hydraulic oil. Generally, when the amount is less than 0.5 parts by weight, the effect is small, and when the amount is more than 7.0 parts by weight, an anti-oxidation effect may be expected, but problems such as discoloration of the oil and deterioration of a flame-retardant effect may be raised. When the amount is included within the above range, a suitable anti-oxidation effect may be obtained, and the occurrence of problems such as inhibition of environmental friendliness (biodegradability and fish toxicity) due to an increase in the amount added may be prevented or reduced.

As for antioxidant power of the antioxidant, it may be confirmed from the experimental results that the more resonance hybrids of electrons are formed, the more excellent the antioxidant power is.

The antioxidant may include at least one or more of phenylnaphthylamine-based, aromatic amines such as alkylated diphenylamine, N-isopropyl-N'-phenyl-1,4-phenylenedi amine (N-phenyl-N'-isopropyl-p-phenylenediamine), and N,N'-di-2-naphthyl-2-phenylenediamine; hydroquinone-based such as mono-tert-butylhydroquinone; phenol-based such as bisphenol 2,2'-metylen-bis-(4-methyl-6-tert-butylphenol), 4,4-butylidenebis(6-tert-butyl-3-methylphenol), and BHT(3,5-di-tert-butyl-4-hydroxytoluene); phosphate ester-based such as Tris (nonylphenyl) Phosphate, and metal salts (Zn-DTP) of phosphate ester; and sulfur-based compounds such as dilauryl thiodipropionate, 2-mercaptobenzoimidazole, and 2-mercaptomethyl benzimidazole, but not limited thereto.

According to an example embodiment, the thickening and viscosity index enhancer may be included in an amount of 0.01 wt % to 5.0 wt % in the flame-retardant hydraulic oil.

The thickening and viscosity index enhancer may be a viscosity enhancer and a viscosity index enhancer, and may include at least one of olefin copolymers of styrene-hydrocarbon polymers such as styrene-butadiene copolymer and styrene-maleate ester copolymer, polybutene, polyisobutylene, and polymethacrylate, polyacrylate, ethylene-propylene copolymer, but not limited thereto.

The thickening and viscosity index enhancer may have a molecular weight of 300 to 10000 in consideration of flame retardancy and environmental friendliness, and the like. When the molecular weight is included in the above range, a hydraulic oil composition having an appropriate viscosity may be provided.

According to an example embodiment, the anti-load and anti-abrasive additive may be included in an amount of 0.01 wt % to 7.0 wt % in the flame-retardant hydraulic oil composition. When the amount is included in the above range, while hydraulic equipment is running, excessive wear of cylinders, pumps, or the like may be prevented to improve a life of equipment and may reduce overheating caused by wear.

The anti-load and anti-abrasive additive may include at least one or more of an amine salt of phosphate ester, aryl phosphate-based, metal salts of phosphate ester, and sulfide additives, but not limited thereto. Preferably, the anti-load and anti-abrasive additive may be an amine salt of phosphate ester.

For example, in the anti-load and anti-abrasive additives, the amine salt-based (Formula 2) of the neutralized phosphate ester has the most excellent effect, and metal salts of phosphate ester; allyl-based phosphate ester, and sulfide additives may be used in combination, and thus a synergistic effect may be exhibited. The compound represented by Formula 2 may have a total acid number (TAN, mgKOH/g, ASTM D664) of 50 higher; 100 higher; or 200 higher.

[Formula 2]

In Formula 2, R represents hydrogen or a C1 to C10 alkyl or aryl type hydrocarbon compound, X represents hydrogen or C1 to C4 hydrocarbon, and n is an integer from 1 to 10.

If necessary, corrosion inhibitors (an azo (azole)-based non-ferrous corrosion inhibitor, a succinic ester type ferrous corrosion inhibitor, a sulfonate (metal-sulfonate)-based corrosion inhibitor, etc.), anti-foaming agents (silicon type, alcohol type, amine type, or polymethacrylate anti-foaming agents), pour point depressants (polymethacrylate type etc.) and other modifiers may be further added, and these amounts may be added in consideration of an appropriate amount and a combination between each component as long as it does not deviate from the aspect of the present disclosure.

Hereinafter, the present disclosure will be described in more detail with reference to examples and comparative examples. However, the following examples are merely illustrative of the present disclosure, and the present disclosure is not limited to these examples.

Example 1: Synthesis of Glycerin-Ester-Based Lubricating Base Oil

Example 1-1

According to Table 1, glycerin (16 wt %) and C10 fatty acid (84 wt %) were added to a reactor filled with an inert gas, and the reaction was performed for 7 to 12 hours while adding an inert gas of 10 to 400 liters at a temperature of 100° C. to 260° C. Free fatty acid (FFA), kinematic viscosity, iodine value and color of the obtained product were measured and shown in Table 1.

Example 1-2

According to Table 1, glycerin (15 wt %) and C10+C12 fatty acid (85 wt %) were applied, and the reaction was performed for 7 to 12 hours while adding an inert gas of 10 to 400 liters at a temperature of 100° C. to 260° C. FFA, kinematic viscosity, iodine value and color of the obtained product were measured and shown in Table 1.

Example 1-3

According to Table 1, glycerin (10 wt %) and C18+C22 fatty acid (90 wt %) were applied, and the reaction was performed for 6 to 10 hours while adding an inert gas of 10 to 500 liters at a temperature of 100° C. to 350° C. FFA, kinematic viscosity, iodine value and color of the obtained product were measured and shown in Table 1.

Example 1-4

According to Table 1, glycerin (9.5 wt %) and C22 fatty acid (90.5 wt %) were applied, and the reaction was performed for 6 to 10 hours while adding an inert gas of 10 to 500 liters at a temperature of 100° C. to 350° C. FFA, kinematic viscosity, iodine value and color of the obtained product were measured and shown in Table 1.

Example 1-5

According to Table 1, glycerin (10.5 wt %) and mixture (89.5 wt %) of C10 to C22 were applied, and the reaction was performed for 6 to 12 hours while adding an inert gas of 10 to 700 liters at a temperature of 100° C. to 350° C.

FFA, kinematic viscosity, iodine value and color of the obtained product were measured and shown in Table 1.

Example 1-6

According to Table 1, glycerin (10.5 wt %) and mixture (89.5 wt %) of C10 to C22 were applied, and the reaction was performed for 6 to 10 hours while adding an inert gas of 10 to 1000 liters at a temperature of 100° C. to 350° C. FFA, kinematic viscosity, iodine value and color of the obtained product were measured and shown in Table 1.

TABLE 1

| Examples | Composition of fatty acid | Free Fatty Acid (FFA) [X1)] | Kinematic viscosity (mm$_2$/s) | Iodine value | Color [X2)] |
|---|---|---|---|---|---|
| Example 1-1 | C10 | 1.0 or lower | 20 | 10 or lower | 3.0 or lower |
| Example 1-2 | C10 + C12 | 1.0 or lower | 22 | 10 or lower | 3.0 or lower |
| Example 1-3 | C18 + C22 | 1.0 or lower | 40 | 90 or lower | 3.0 or lower |
| Example 1-4 | C22 | 1.0 or lower | 45 | 90 or lower | 3.0 or lower |
| Example 1-5 | Mixture of C10 to C22 (C18 content of 75% or higher) | 1.0 or lower | 40 | 100 or lower | 3.0 or lower |
| Example 1-6 | Mixture of C10 to C22 (C18 content of 85% or higher) | 1.0 or lower | 40 | 90 or lower | 3.0 or lower |

[X1)] is a total acid number of a lubricating base oil and defined as % as Oleic.
[X2)] means a color grade specified in ASTM D 1500.

Example 2: Preparation of Environmental-Friendly Hydraulic Oil

The glycerin-ester-based lubricating base oil prepared in Example 1, an additive, and other additives were blended according to the components and contents (unit: parts by weight) shown in Table 2 to prepare a hydraulic oil composition. Physical properties and performance of the prepared hydraulic oil composition were measured and shown in Table 2.

TABLE 2

| | | | Example 2-1 | Example 2-2 | Example 2-3 | Example 2-4 | Example 2-5 | Example 2-6 | Example 2-7 | Example 2-8 |
|---|---|---|---|---|---|---|---|---|---|---|
| Hydraulic oil | Lubricating base oil | Example 1-1 | 94.2 | | | 50.0 | | | | |
| | | Example 1-2 | | 94.6 | | | | | | |
| | | Example 1-3 | | | 44.6 | | | | 34.6 | |
| | | Example 1-4 | | | | | 94.6 | | 55.0 | |
| | | Example 1-5 | | | | | | 94.6 | | 34.6 |
| | | Example 1-6 | | | | | | 93.0 | | 55.0 |
| | Antioxidant | | 1.0 | 1.0 | 1.0 | 1.5 | 1.5 | 2.0 | 3.0 | 3.0 |
| | Anti-abrasive additive | | 1.0 | 1.0 | 1.0 | 0.5 | 0.5 | 1.0 | 2.2 | 2.2 |
| | Thickener | | 2.5 | 1.5 | 1.5 | 2.0 | 2.0 | 1.0 | 3.0 | 3.0 |
| | Corrosion inhibitor | | 0.2 | 0.2 | 0.2 | 0.1 | 0.1 | 0.1 | 0.5 | 0.5 |
| | Antifoaming agent | | 0.1 | 0.2 | 0.2 | 0.1 | 0.1 | 0.1 | 0.2 | 0.2 |
| | Others | | 1.0 | 1.5 | 1.5 | 1.2 | 1.2 | 1.5 | 0.5 | 0.5 |
| Physical properties and performance | Flash point (° C.) | | 250 or higher | 250 or higher | 250 or higher | 300 or higher | 300 or higher | 300 or higher | 300 or higher | 300 or higher |
| | Viscosity index | | 150 or higher | 150 or higher | 150 or higher | 200 or higher | 200 or higher | 200 or higher | 200 or higher | 200 or higher |
| | Oxidation stability [X1)] | | 400 min. or longer | 400 min. or longer | 400 min. or longer | 300 min. or longer | 250 min. or longer | 250 min. or longer | 250 min. or longer | 250 min. or longer |
| | Abrasion resistance [X2)] | | 0.5 mm or lower | 0.5mm or lower | 0.5mm or lower | 0.5mm or lower | 0.5mm or lower | 0.5mm or lower | 0.5mm or lower | 0.5mm or lower |
| | Anti-load [X3)] | | 126 or higher | 126 or higher | 160 or higher | 160 or higher | 160 or higher | 200 or higher | 200 or higher | 160 or higher |
| | Friction coefficient [X4)] | | 0.10 or lower | 0.10 or lower | 0.10 or lower | 0.10 or lower | 0.10 or lower | 0.10 or lower | 0.10 or lower | 0.10 or lower |

In the above, the lubricating base oil was selected in consideration of viscosity grade of the hydraulic oil, and test equipment and test method used in each performance evaluation are as follows.
[X1)] Tester: Rotating bomb oxidation stability tester, Test method: ASTM D2272
[X2)] Tester: Shell-type four-ball tester (1200 rpm, 40 kg/cm$^2$), Test method: ASTM D 2266
[X3)] Tester: Shell-type four-ball tester (1760 rpm, kg/cm$^2$), Test method: ASTM D 2596
[X4)] Tester: SRV Test (1 mm, 200N, 40° C., 50 Hz)

Figure 1:
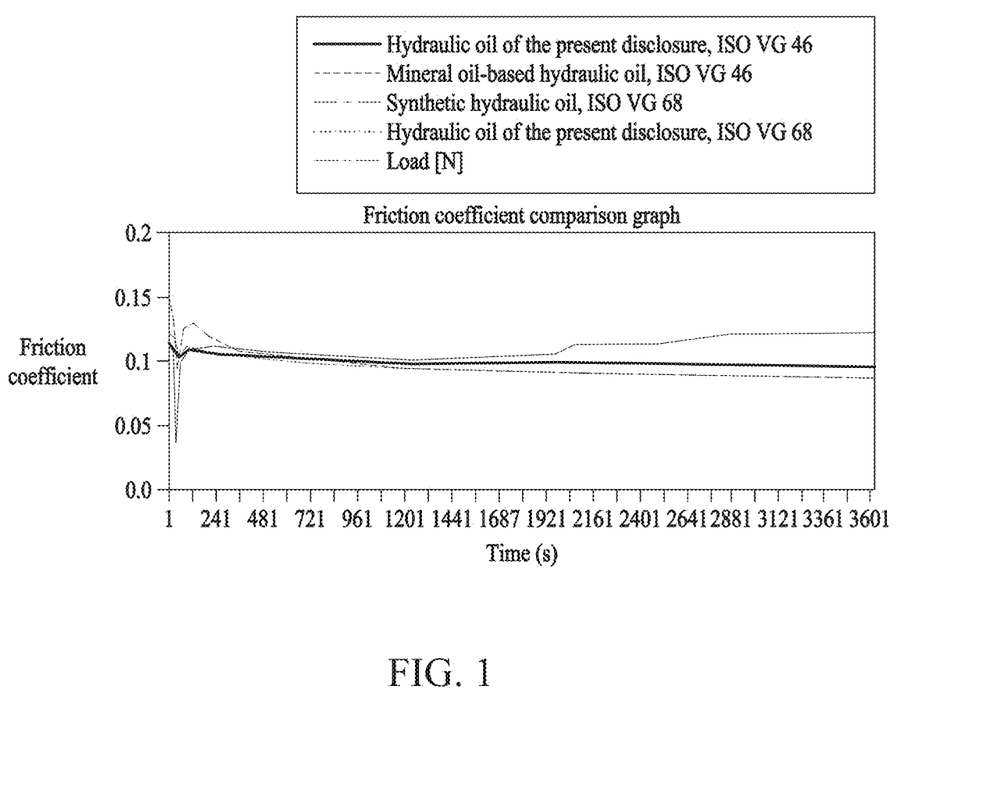
FIG. 1 illustrates a result of measuring SRV friction coefficients of the hydraulic oils prepared in Examples of the present disclosure, mineral-based hydraulic oils, and commercially available hydraulic oils according to an example embodiment of the present disclosure.

(1) Comparison of SRV Friction Coefficient Between Hydraulic Oils of Example 2 and Mineral Oil-Based Hydraulic Oil SRV (1 mm, 200 N, 40° C., 50 Hz) friction coefficient of hydraulic oil and mineral oil-based hydraulic oil was compared and shown in FIG. 1. Mineral oil-based and synthetic hydraulic oils are anti-abrasive hydraulic oils available in the general market. That is, the hydraulic oils are suitable for International viscosity specification (ISO VG) 46 and 68 made by API Standard Group II lubricating base oil.

Referring to Table 2 and FIG. 1, it is obtained from Table 2 that the hydraulic oil to which the vegetable-based lubricating base oil according to the present disclosure is applied has good results in flash point, viscosity index, and oxidation stability, and has very excellent results in SRV test (friction, wear, vibration) for the hydraulic oil, and it is shown in FIG. 1 to corresponds to a very excellent and stable result compared to general mineral oil-based hydraulic oils. The environmental-friendly hydraulic oil according to the present disclosure may be expected to be more stable and energy-saving effect when applied to actual industrial equipment.

(2) Biodegradability (Biodegradable) Measurement

In order to confirm environmental friendliness of Example 2, biodegradability was measured and shown in Table 3.

TABLE 3

| Biodegradability | | Measuring method |
| --- | --- | --- |
| When contents of lubricating base oils 1 and 2 of the lubricating base oil according to the present disclosure are 90% or higher [Example 2-1], [Example 2-2] | 65% or higher | OECD ready biodegradation 301b, Modified MiTi Test(1) |
| When contents of lubricating base oils 3, 4, 5, and 6 of the lubricating base oil according to the present disclosure is 90% or higher [Example 2-4], [Example 2-5], [Example 2-6] [Example 2-7], [Example 2-8] | 80% or higher | |
| When contents of lubricating base oils 3, 4, 5 and 6 in the mixture of lubricating base oils 1 and 2 and lubricating base oils 3, 4, 5 and 6 of the lubricating base oil according to the present disclosure are 50% or higher [Example 2-3] | 65% to 80% | |

Referring to Table 3, it can be seen that when the vegetable glycerin-ester-based lubricating base according to the present disclosure is applied, biodegradability is excellent, so that environmental-friendly hydraulic oil may be provided.

Example embodiments of the present disclosure may provide a hydraulic oil (lubricating oil) which has a good affinity for a human body because biodegradation by microorganisms is possible, and the composition has excellent physical properties, so as to contribute to substantial cost reduction because it has a low risk of fire due to its flame retardancy, as well as an energy saving effect, extension of tool life, an increase in an efficiency of equipment operation, and a reduction in an equipment consumable replacement cycle, even when equipment is driven in industrial sites, so as to respond to regulation of carbon emission.

2. Synthesis Example

A synthetic vegetable oil (glycerin-ester) was prepared as follows.

Lubricating Base Oil A

Glycerin (16.0 wt %) and mixed fatty acid (84 wt %) of total C36 (C10 to C14) were applied, and the reaction was performed for 6 to 12 hours while adding an inert gas of 10 to 700 liters at a temperature of 100° C. to 300° C. FFA, kinematic viscosity and iodine value of the obtained product were measured and shown in Table 4.

Lubricating Base Oil B

Glycerin (15.0 wt %) and mixed fatty acid (85 wt %) of total C42 (C10 to C16) were applied, and the reaction was performed for 6 to 12 hours while adding an inert gas of 10 to 700 liters at a temperature of 100° C. to 300° C. FFA, kinematic viscosity and iodine value of the obtained product were measured and shown in Table 4.

Lubricating Base Oil C

Glycerin (14.5 wt %) and mixed fatty acid (85.5 wt %) of total C48 (C14 to C18) were applied, and the reaction was performed for 6 to 12 hours while adding an inert gas of 10 to 700 liters at a temperature of 100° C. to 300° C. FFA, kinematic viscosity and iodine value of the obtained product were measured and shown in Table 4.

Lubricating Base Oil D

Glycerin (13.5 wt %) and mixed fatty acid (86.5 wt %) of total C50 (C14 to C18) were applied, and the reaction was performed for 6 to 12 hours while adding an inert gas of 10 to 700 liters at a temperature of 100° C. to 300° C. FFA, kinematic viscosity and iodine value of the obtained product were measured and shown in Table 4.

Lubricating Base Oil E

Glycerin (13.5 wt %) and mixed fatty acid (86.5 wt %) of total C50 (C14 to C18) were applied, and the reaction was performed for 6 to 12 hours while adding an inert gas of 10 to 700 liters at a temperature of 100° C. to 300° C. FFA, kinematic viscosity and iodine value of the obtained product were measured and shown in Table 4.

Lubricating Base Oil F

Glycerin (12.5 wt %) and mixed fatty acid (87.5 wt %) of total C54 (C14 to C22) were applied, and the reaction was performed for 6 to 12 hours while adding an inert gas of 10 to 700 liters at a temperature of 100° C. to 320° C. FFA, kinematic viscosity and iodine value of the obtained product were measured and shown in Table 4.

Lubricating Base Oil G

Glycerin (12.0 wt %) and mixed fatty acid (88.0 wt %) of total C54 (C14 to C22) were applied, and the reaction was performed for 6 to 12 hours while adding an inert gas of 10 to 700 liters at a temperature of 100° C. to 320° C. FFA, kinematic viscosity and iodine value of the obtained product were measured and shown in Table 4.

Lubricating Base Oil H

Glycerin (11.0 wt %) and mixed fatty acid (89.0 wt %) of total C54 (C14 to C22) were applied, and the reaction was performed for 6 to 12 hours while adding an inert gas of 10 to 1000 liters at a temperature of 100° C. to 350° C. FFA, kinematic viscosity and iodine value of the obtained product were measured and shown in Table 4.

Lubricating Base Oil I

Glycerin (10.0 wt %) and mixed fatty acid (90.0 wt %) of total C60 (C16 to C22) were applied, and the reaction was performed for 6 to 12 hours while adding an inert gas of 10 to 1000 liters at a temperature of 100° C. to 350° C. FFA, kinematic viscosity and iodine value of the obtained product were measured and shown in Table 4.

Lubricating Base Oil J

Glycerin (9.5 wt %) and mixed fatty acid (90.5 wt %) of total C66 (C18 to C22) were applied, and the reaction was performed for 6 to 12 hours while adding an inert gas of 10 to 1000 liters at a temperature of 100° C. to 350° C. FFA, kinematic viscosity and iodine value of the obtained product were measured and shown in Table 4.

TABLE 4

| Classification of lubricating base oil | Total carbon number of fatty acid | Free Fatty Acid (FFA)[X.1] | Kinematic viscosity (mm$_2$/s) | Iodine values |
|---|---|---|---|---|
| Lubricating base oil A | 36 | 0.7 | 21.5 | 15 |
| lubricating base oil B | 42 | 0.7 | 24.8 | 20 |
| lubricating base oil C | 48 | 0.6 | 28.5 | 26 |
| lubricating base oil D | 50 | 0.6 | 30.3 | 30 |
| lubricating base oil E | 50 | 0.6 | 31.5 | 65 |
| lubricating base oil F | 54 | 0.5 | 33.6 | 40 |
| lubricating base oil G | 54 | 0.5 | 35.4 | 65 |
| lubricating base oil H | 54 | 0.5 | 38.5 | 80 |
| lubricating base oil I | 60 | 0.4 | 41.5 | 75 |
| lubricating base oil J | 66 | 0.3 | 45.0 | 72 |

[X.1] is a content of the unreacted fatty acid of the lubricating base oil, and defined as "% as Oleic".

2. Preparation of Additive

Flame-retardant additives, antioxidants, and anti-load and anti-abrasive additives shown in each of Tables 5 to 8 were prepared.

TABLE 5

| Types of flame-retardant | |
|---|---|
| Flame-retardant additive A | Tricresyl Phosphate |
| Flame-retardant additive B | Tributyl Phosphate |
| Flame-retardant additive C | Tris (β-chloroethyl) Phosphate |
| Flame-retardant additive D | Tris (β-chloropropyl) Phosphate |
| Flame-retardant additive E | Tris (1,3-dichloro-2-propyl) Phosphate (Tris (dichloropropyl) Phosphate) |
| Flame-retardant additive F | Trioctyl Phosphate |
| Flame-retardant additive G | Triphenyl Phosphate |
| Flame-retardant additive H | Octyl diphenyl Phosphate |
| Flame-retardant additive I | Tris (Isopropylphenyl) Phosphate |
| Flame-retardant additive J | Tributoxyethyl Phosphate |

TABLE 6

| Types of Antioxidant | |
|---|---|
| Antioxidant A | Phenylnaphtylamine-based |
| Antioxidant B | Alkylated diphenylamine-based |
| Antioxidant C | N-isopropyl-N'-phenyl-1,4-phenylenediamine (N-phenyl-N'-isopropyl-P-phenylenediamine) |
| Antioxidant D | N,N'-di-2-naphthyl-2- phenylenediamine |
| Antioxidant E | mono-tert-butylhydroquinone |
| Antioxidant F | Bisphenol 2,2'- Metylen-Bis-(4-methyl-6-Tert-Butylphenol) |
| Antioxidant G | 4,4-butylidenebis (6-tert-butyl-3-methylphenol) |
| Antioxidant H | 2-mercaptomethyl benzimidazole |
| Antioxidant I | Tris (nonylphenyl) phosphite (Tris (nonylphenyl) phosphate) |
| Antioxidant J | Dilauryl Thiodipropionate |

TABLE 7

| Types of anti-load and anti-abrasive additive | |
|---|---|
| Anti-load and anti-abrasive additive A | Amine salt of phosphate ester (TAN 50, having a ferrous corrosion inhibitor) |
| Anti-load and anti-abrasive additive B | Amine salt of phosphate ester (TAN 100, having a ferrous corrosion inhibitor) |
| Anti-load and anti-abrasive additive C | Amine salt of phosphate ester (TAN 150, having no corrosion inhibitor) |
| Anti-load and anti-abrasive additive D | Amine salt of phosphate ester (TAN 200, having no corrosion inhibitor) |
| Anti-load and anti-abrasive additive E | Metal salt (zinc compound) of phosphate ester |
| Anti-load and anti-abrasive additive F | Metal salt (molybdenum compound) of phosphate ester |
| Anti-load and anti-abrasive additive G | Sulfide (sulfur content of 10 to 12%, vegetable oil, inactivity) |
| Anti-load and anti-abrasive additive H | Sulfide (sulfur content of 14 to 16%, vegetable oil, inactivity) |

Examples 3-1 to 3-14

(1) Preparation of Flame-Retardant Hydraulic Oil Composition

The synthetic vegetable oil (glycerin-ester) of Table 4 was used as the lubricating base oil, and flame-retardant additives (Table 5), antioxidants (Table 6), and anti-load and anti-abrasive additives (Table 7) were mixed to prepare a flame-retardant hydraulic oil composition. Specific compositions were shown in Tables 8 and 9.

TABLE 8

| Compositions | Example 3-1 | Example 3-2 | Example 3-3 | Example 3-4 | Example 3-5 | Example 3-6 | Example 3-7 |
|---|---|---|---|---|---|---|---|
| Lubricating base oil A | 25.0 | 17.0 | | | | | |
| Lubricating base oil B | | | 15.5 | | | | |
| Lubricating base oil C | | | 77.0 | 33.0 | 25.5 | | |
| Lubricating base oil H | 67.0 | | | 61.5 | | 94.0 | |
| Lubricating base oil I | | 73.5 | | | | | 45.0 |
| Lubricating base oil J | | | | | 70.0 | | 49.0 |
| Flame-retardant additive A | 2.0 | 2.5 | | | | 1.0 | 2.5 |
| Flame-retardant additive B | | | 2.0 | | | | |
| Flame-retardant additive F | | | | | | 1.0 | |
| Flame-retardant additive G | | | | 2.5 | | | |
| Flame-retardant additive H | | | | | 1.5 | | |
| Antioxidant A | 1.2 | 1.5 | | | 0.5 | | 1.0 |
| Antioxidant B | | | 1.5 | | 0.5 | | 0.5 |

TABLE 8-continued

| Compositions | | Example 3-1 | Example 3-2 | Example 3-3 | Example 3-4 | Example 3-5 | Example 3-6 | Example 3-7 |
|---|---|---|---|---|---|---|---|---|
| Antioxidant D | | | | | 1.5 | | 1.0 | |
| Antioxidant G | | | | | | | 0.5 | |
| Anti-load/anti-abrasive additive A | | 1.0 | | | 0.5 | 1.0 | 0.5 | 0.5 |
| Anti-load/anti-abrasive additive B | | | | 1.0 | | | 0.5 | |
| Anti-load/anti-abrasive additive E | | | 1.0 | | 0.5 | | | |
| Thickening/viscosity index enhancer | | Suitable | Suitable | Suitable | Suitable | Suitable | Suitable | Suitable |
| Corrosion inhibitor | | Suitable | Suitable | Suitable | Suitable | Suitable | Suitable | Suitable |
| Pour point depressant | | Suitable | Suitable | Suitable | Suitable | Suitable | Suitable | Suitable |
| Others | | Suitable | Suitable | Suitable | Suitable | Suitable | Suitable | Suitable |
| Oxidation stability (RPVOT) | | Life time: 200 min. or longer | | | | | | |
| Flame retardancy | Hot Manifold test | Extinguished immediately after ignition | | | | | | |
| | Sprayed fire test | Not burn continuously | | | | | | |
| Lubricity | SRV test (Friction Coefficient) | 0.110 or lower | | | | | | |
| | SRV test (Extreme pressure) | 2000N or higher | | | | | | |
| | Shell 4-ball (Abrasion resistance) | Scar diameter: 0.45 mm or lower | | | | | | |
| | Shell 4-ball (Extreme pressure) | 126 kgf or higher | | | | | | |
| Fish toxicity (Daphnia magna test) | | 100 or higher | | | | | | |

TABLE 9

| Compositions | | Example 3-8 | Example 3-9 | Example 3-10 | Example 3-11 | Example 3-12 | Example 3-13 | Example 3-14 |
|---|---|---|---|---|---|---|---|---|
| Lubricating base oil B | | 20.0 | | | | | | |
| Lubricating base oil D | | | 22.5 | | | | | |
| Lubricating base oil G | | | | 70.0 | | | | |
| Lubricating base oil H | | 74.0 | | | 60.0 | | | |
| Lubricating base oil I | | | 72.5 | | 35.5 | 95.0 | | 45.0 |
| Lubricating base oil J | | | | 24.0 | | | 95.0 | 49.0 |
| Flame-retardant additive A | | 2.0 | 1.5 | | | 1.0 | 1.0 | 2.0 |
| Flame-retardant additive C | | | 1.0 | | | | 1.0 | |
| Flame-retardant additive D | | | | | 1.5 | | | |
| Flame-retardant additive I | | | | | | 1.5 | | |
| Flame-retardant additive J | | | 2.0 | | | | | |
| Antioxidant A | | 0.5 | | 0.5 | | 0.5 | | 1.0 |
| Antioxidant E | | 0.5 | 0.5 | | 1.0 | 0.5 | | 0.5 |
| Antioxidant G | | | | 0.5 | | | 1.0 | |
| Antioxidant I | | | 0.5 | | | | 0.5 | |
| Anti-load/anti-abrasive additive C | | 0.5 | | | 0.5 | | | 0.5 |
| Anti-load/anti-abrasive additive E | | | 1.0 | | 0.5 | | 0.5 | |
| Anti-load/anti-abrasive additive G | | 0.5 | | 0.5 | | 0.5 | | 0.5 |
| Thickening/viscosity index enhancer | | Suitable | Suitable | Suitable | Suitable | Suitable | Suitable | Suitable |
| Corrosion inhibitor | | Suitable | Suitable | Suitable | Suitable | Suitable | Suitable | Suitable |
| Pour point depressant | | Suitable | Suitable | Suitable | Suitable | Suitable | Suitable | Suitable |
| Others | | Suitable | Suitable | Suitable | Suitable | Suitable | Suitable | Suitable |
| Oxidation stability (RPVOT) | | Life time: 200 min. or longer | | | | | | |
| Flame retardancy | Hot Manifold test | Extinguished immediately after ignition | | | | | | |
| | Sprayed fire test | Not burn continuously | | | | | | |
| Lubricity | SRV test (Friction Coefficient) | 0.110 or lower | | | | | | |
| | SRV test (Extreme pressure) | 2000N or higher | | | | | | |
| | Shell 4-ball | Scar diameter: 0.45 mm or lower | | | | | | |

TABLE 9-continued

| Compositions | Example 3-8 | Example 3-9 | Example 3-10 | Example 3-11 | Example 3-12 | Example 3-13 | Example 3-14 |
|---|---|---|---|---|---|---|---|
| (Abrasion resistance) Shell 4-ball (Extreme pressure) | | | | 126 kgf or higher | | | |
| Fish toxicity (Daphnia magna test) | | | | 100 or higher | | | |

TABLE 10

| Test items | | Test methods |
|---|---|---|
| Fish toxicity (Daphnia magna test) | | Daphnia magna acute toxicity test: 48 h EC50 Compliance with OECD TG 202 |
| Oxidation stability (RPVOT) | | Rotating bomb oxidation test (ASTM D 2272) |
| Flame retardancy test | Hot Manifold test | Drop the sample on a manifold that reached 374° C. to check for ignition |
| | Sprayed fire test | High-pressure spray ignition experiment-the Machinery Promotion Association Technology Research Institute Act (Japan) |
| Lubricity test | SRV test Friction Coefficient | Measurement of Friction Coefficient using a SRV tester (Test conditions: 1 mm, 200N, 40° C., 50 Hz) |
| | SRV test Extreme pressure | Measurement of extreme pressure using a SRV tester (Test conditions: 2 mm, 40° C., 50 Hz, increase by 100N) |
| | Shell 4-Ball Abrasion resistance | Abrasion resistance using a Shell 4-Ball tester (Test conditions: 1200 rpm, 40 kgf, 75° C., 1 hrs) |
| | Shell 4-Ball Extreme pressure | Extreme pressure using a Shell 4-Ball tester (Test conditions: 1720 rpm, room temperature, 10 s) |

(1) Evaluation of Physical Properties

Physical properties and performance were measured in accordance with test conditions such as fish toxicity, oxidation stability, flame retardancy, and lubricity of the flame-retardant hydraulic oil compositions prepared according to Table 10 and the results were shown in Tables 8 to 9.

(2) Sprayed Fire Test Result

Figure 2A:
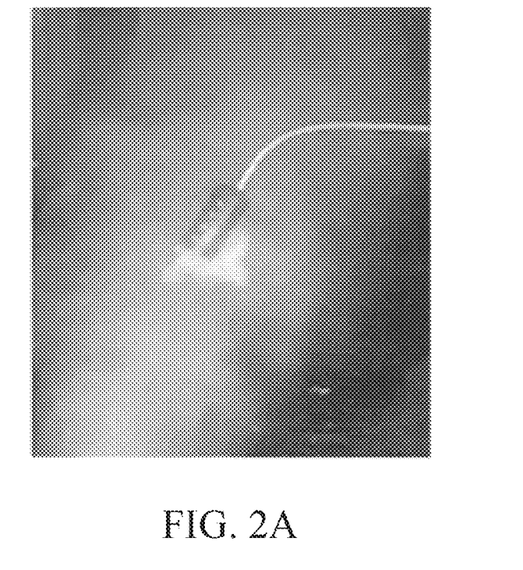
FIG. 2A illustrates a comparative result of flame retardancy by a sprayed fire test of the hydraulic oil compositions prepared in Examples of the present disclosure, according to an example embodiment of the present disclosure.
Figure 2B:
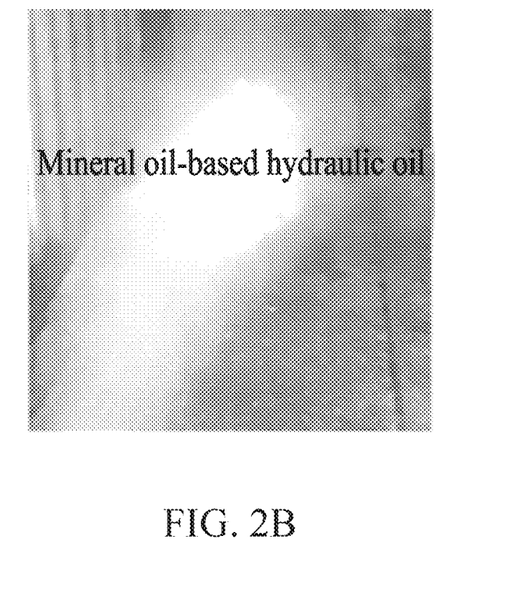
FIG. 2B illustrates a result of flame retardancy by a sprayed fire test of commercially available mineral-based hydraulic oils, according to an example embodiment of the present disclosure.

A sprayed fire test was performed according to high-pressure spray ignition experiment—the Machinery Promotion Association Technology Research Institute Act (Japan), and is shown in FIG. 2. FIG. 2 shows images of Examples 3 to 7 and a commercially available petroleum-based product.

(3) Measurement of Electricity Consumption According to Use of Hydraulic Oil

Figure 3:
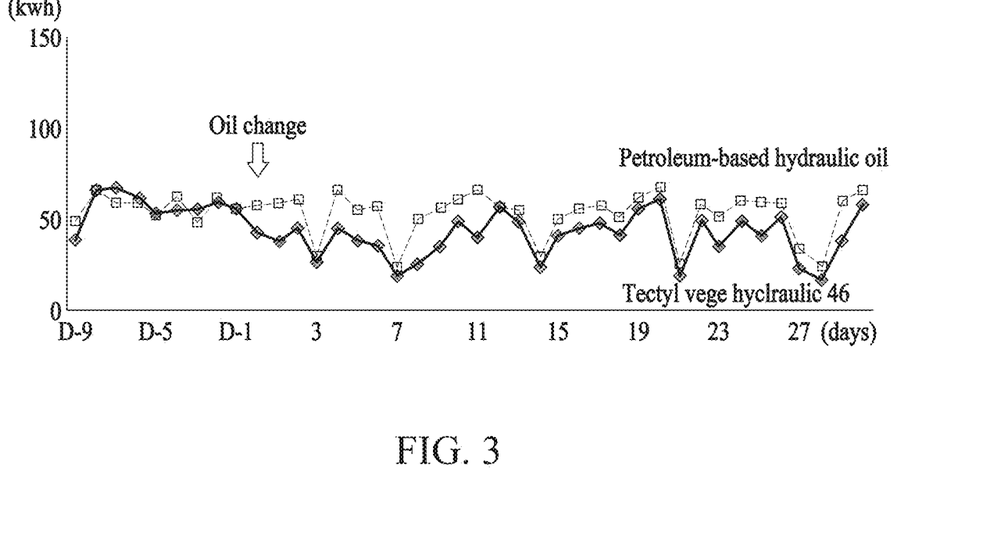
FIG. 3 illustrates a result of measuring electricity consumption by using the hydraulic oil compositions prepared in Examples of the present disclosure, and commercially available mineral-based hydraulic oils according to an example embodiment of the present disclosure.

The hydraulic oil was changed to Examples 3-14 and a mineral oil-based commercial product, and change of electricity consumption was measured and shown in FIG. 3.

Test Equipment: 850 Tons Die Casting

Referring to Tables 8 to 9, with respect to the environmental-friendly flame-retardant hydraulic oil prepared by adding the synthetic vegetable oil (glycerin-ester) according to the present disclosure as the lubricating base oil, and a flame-retardant additive, an antioxidant, a thickening and viscosity index enhancer, an anti-load and anti-abrasive enhancer, a corrosion inhibitor, a pour point depressant, and other modifiers, excellent results in fish toxicity (daphnia magna test) test were obtained, excellent flame retardancy performance was achieved, very excellent results in the SRV test (friction, wear, vibration) and Shell 4-Ball test for the hydraulic oil were achieved, and very good result in anti-oxidant performance was also obtained.

From the results of FIG. 2, it may be seen that the environmental-friendly flame-retardant hydraulic oil according to the present disclosure was not burned, but the mineral oil-based hydraulic oil causes an explosive fire.

From the results of FIG. 3, it may be seen that the environmental-friendly flame-retardant hydraulic oil according to the present disclosure may reduce an average of 7.12% in change of electricity consumption compared to petroleum-based hydraulic oils. This means that the environmental-friendly flame-retardant hydraulic oil according to the present disclosure may be expected to be more stable and energy-saving effect when applied to actual industrial equipment.

It is necessary that an environmental friendly hydraulic oil used in equipment is not only a standard for environmental friendliness for biodegradability and fish toxicity, but also allow to reduce the amount of electricity consumed while equipment is driven, so that it may support stable contributions to carbon credits, but there have been no cases of actual evaluation results on reduction in electricity consumption in the reported hydraulic oils. However, when electric energy consumed, when the synthetic vegetable hydraulic oil according to the present disclosure was applied to an industrial site, is compared with that of mineral oil-based anti-abrasive hydraulic oil (ISO VG 46 of ISO-L-HM specification) of the related art, an average of about 7.12% of savings may be obtained (FIG. 3), and this shows that it is possible to provide a hydraulic oil capable of actively coping with energy reduction and ensuring stable operation of equipment according to the present disclosure.

Example embodiments of the present disclosure may provide a hydraulic oil composition by adding a synthetic vegetable oil (glycerin-ester) prepared using fatty acid and glycerin through a catalyst-free and rinsing-free process, and by blending lubricating additives further improved and developed in comparison with the related art, such as a flame-retardant additive, an antioxidant, an anti-load and anti-abrasive enhancer, a thickening and viscosity index enhancer, a pour point depressant, a corrosion inhibitor, and other modifiers herewith. The hydraulic oil composition may contribute to a substantial cost reduction associated with an energy reduction by reducing carbon emissions due to a reduction in electric energy consumption in a process of using a hydraulic oil (lubricating oil), may also guarantee expansion of an application area as a hydraulic oil and extension of a service life, and may significantly reduce a risk of fire by checking flame retardancy.

Furthermore, the present disclosure may actively cope with emphasis on an affinity for the natural environment and humans, energy reduction measures, and guarantee of a stable operation of equipment required in a process of industrial development, may also reduce a risk of fire by imparting flame retardancy, and may contribute to a substantial cost reduction due to its price competitiveness with mineral oil-based lubricating oils.

As described above, while a few example embodiments have been described with reference to certain drawings, it will be apparent to those skilled in the art that various technical modifications and variations may be made from the foregoing descriptions. For example, adequate effects may be achieved even if the foregoing processes and methods are carried out in different orders than described above, and/or the aforementioned elements, such as systems, structures, devices, or circuits are combined or coupled in different forms and modes than as described above or be substituted or switched with other components or equivalents.

Thus, other implementations, alternative embodiments and equivalents to the claimed subject matter are construed as being within the appended claims.

The invention claimed is:

1. A method of preparing a glycerin-ester-based lubricating base oil, the method comprising:
adding a fatty acid-containing material and a glycerin-containing material to a reactor, and
synthesizing a glycerin-ester in an inert gas atmosphere and at a reaction temperature of 100° C. to 350° C. in the reaction and the reaction temperature has a plurality of temperature sections comprising at least one of a first temperature section of 100° C. to 180° C., a second temperature section of 200° C. to 230° C., and a third temperature section of 250° C. to 350° C.,
wherein the method is a catalyst-free and rinsing-free process.

2. The method of claim 1, wherein
an amount of the inert gas to be added ranges from 10 liters to 1000 liters per minute, based on a synthesis amount of 10000 liters, and
the amount of the inert gas to be added is adjusted depending on the temperature sections.

3. The method of claim 2, wherein
the reaction temperature is raised to 50° C. when a free fatty acid (FFA) content is reduced by 50%, and
the amount of the gas to be added is increased by 50% or more when the FFA content is reduced by 50%.

4. The method of claim 3, wherein the synthesizing of the glycerin-ester terminates a synthesis when the FFA content is 1.0 or less or 0.5 or less.

5. The method of claim 1, wherein the fatty acid-containing material is extracted from a natural vegetable oil, and contains one or more of C10 to C22 fatty acids.

6. The method of claim 1, wherein the glycerin-ester is represented by the following Formula 1:

[Formula 1]

wherein $R_1$, $R_2$ and $R_3$ are each a C8 to C20 saturated or unsaturated fatty acid residue.

* * * * *